United States Patent
Masiz et al.

(10) Patent No.: US 6,635,274 B1
(45) Date of Patent: Oct. 21, 2003

(54) SOLUTION-BASED TRANSDERMAL DRUG DELIVERY SYSTEM

(75) Inventors: John J. Masiz, Topsfield, MA (US); Stephen G. Carter, Andover, MA (US)

(73) Assignee: BioChemics, Inc., Danvers, MA (US)

( * ) Notice: Subject to any disclaimer, the term of this patent is extended or adjusted under 35 U.S.C. 154(b) by 0 days.

(21) Appl. No.: 09/698,483

(22) Filed: Oct. 27, 2000

(51) Int. Cl.⁷ .............................. A61F 13/00; A61K 9/70
(52) U.S. Cl. ........................................ 424/449; 424/447
(58) Field of Search .................................. 424/449, 447

(56) References Cited

U.S. PATENT DOCUMENTS

| | | | |
|---|---|---|---|
| 4,386,095 A | 5/1983 | Gibson et al. ............... | 424/263 |
| 4,440,777 A | 4/1984 | Zupan ......................... | 424/274 |
| 4,562,196 A | 12/1985 | Horn et al. .................. | 514/332 |
| 4,695,465 A | 9/1987 | Kigasawa et al. .......... | 424/449 |
| 4,721,619 A | 1/1988 | Panoz et al. ................. | 424/459 |
| 4,894,240 A | 1/1990 | Geoghegan et al. ........ | 424/497 |
| 4,933,184 A * | 6/1990 | Tsuk ........................... | 424/449 |
| 4,946,853 A | 8/1990 | Bannon et al. .............. | 514/343 |
| 5,229,130 A * | 7/1993 | Sharma et al. .............. | 424/449 |
| 5,370,879 A | 12/1994 | Masterson et al. .......... | 424/490 |
| 5,460,821 A | 10/1995 | Masiz .......................... | 424/449 |
| 5,645,854 A | 7/1997 | Masiz .......................... | 424/449 |
| 5,853,751 A | 12/1998 | Masiz .......................... | 424/449 |
| 5,900,249 A | 5/1999 | Smith .......................... | 424/443 |
| 6,019,988 A * | 2/2000 | Parab et al. ................. | 424/400 |

FOREIGN PATENT DOCUMENTS

| | | |
|---|---|---|
| EP | 0 113 562 | 7/1984 |
| EP | 0 117 027 | 8/1984 |
| EP | 0 156 077 | 10/1985 |
| EP | 0 325 843 | 8/1989 |

* cited by examiner

*Primary Examiner*—Thurman K. Page
*Assistant Examiner*—Rachel M. Bennett
(74) *Attorney, Agent, or Firm*—Nields & Lemack

(57) ABSTRACT

An efficient transdermal delivery system for delivering an active ingredient to the blood supply of a living body, comprising a vasodilator, an active ingredient, and a permeation enhancer for the active ingredient. The components of this mixture are combined in a manner that dissolves them into solution, eliminating the need for a polymeric binding agent and thus diminishing the total molecular weight of the mixture and increasing the penetration and delivery efficiency of the active drug molecules.

5 Claims, No Drawings

SOLUTION-BASED TRANSDERMAL DRUG DELIVERY SYSTEM

BACKGROUND OF THE INVENTION

Transdermal drug delivery offers many advantages over other types of drug delivery. These advantages include improved local, specific drug delivery; avoiding the gastrointestinal complications caused by oral delivery, and improved efficacy and safety profiles for the drugs. While the process of transdermal drug delivery offers these and other advantages, a system that can quickly, precisely and reliably deliver predictable quantities of a wide spectrum of different drug molecules through the skin has is heretofore not been developed.

The evolution of transdermal drug delivery has centered around patch technology. Patch technology is based on the ability to hold an active ingredient in constant contact with the epidermis over substantial periods of time, certain drug molecules, held in such a state, will eventually transfer from the patch into the skin and to a small and variable degree, into the bloodstream. Thus, patch technology relies on the ability of the human body to passively pick up drug molecules through the skin. Transdermal drug delivery using patch technology has recently been applied for delivery of nicotine, in an effort to assist smokers in quitting, the delivery of nitroglycerine to angina sufferers, the delivery of replacement hormones (e.g., estrogen, progesterone and testosterone) and for the delivery of scopolamine for motion sickness. These drug delivery systems comprise a patch with an active ingredient such as a drug incorporated therein, the patch also includes an adhesive for attachment to the skin so as to place the active ingredient in close proximity to the skin.

Problems with patch technology abound. First, most active drug molecules (with the exception of those previously listed) have difficulty passing through the skin, as the skin tissue poses a significant barrier. In fact, in order for a drug molecule to reach the bloodstream, it must pass through the stratum corneum (an especially dense layer of cells), the dermis tissue layer and finally through the wall of the blood vessel. Second, real world conditions such as the patient's obesity, metabolism and circulatory efficiency can effectively inhibit the efficiency of patch-based transdermal drug delivery. Third, patch technology can be used only for conditions involving long, non-acute treatment periods, since the typical transport rate of drug molecules is typically so slow and variable. Finally, patch adhesion to the skin may cause extensive skin trauma as well as cosmetic problems. Specifically, most adhesives currently used tend to aggressively adhere to the skin in a manner that their removal may cause irritation and trauma. Indeed, subsequent patches used by a given individual are often applied to a different area of the skin in order to minimize such irritation and trauma to the skin.

In an effort to enhance the efficiency of transdermal drug delivery, the prior art teaches that by mixing certain individual ingredients (penetration enhancers) with a drug molecule, the ability of the drug molecule to pass through the skin is increased somewhat. For example, U.S. Pat. No. 4,933,184 discloses the use of menthol as a penetration enhancer; U.S. Pat. No. 5,229,130 discloses the use of vegetable oil (soybean and/or coconut oil) as a penetration enhancer; and U.S. Pat. No. 4,440,777 discloses the use of eucalyptol as a penetration enhancer.

Although mixing a penetration enhancer with a drug molecule helps to somewhat increase the speed and efficiency of drug delivery into the skin, problems are still present. First, the aforementioned penetration enhancers constitute a passive, not an active, transport system. Penetration enhancers may improve the transportation of the drug through the outer layers of skin and into the lower skin tissue but they do not significantly enhance the second stage of transfer through the wall of the blood vessel and into the bloodstream. Second, since penetration enhancers are not chemically linked to the drug molecule, the transport of the penetration enhancer into the skin does not necessarily mean that the drug molecule has penetrated into the skin.

U.S. Pat. Nos. 5,460,821, 5,645,854 and 5,853,751 disclose efficient transdermal drug, delivery systems created by combining penetration enhancers, chemical vasodilators, active drug ingredients and a binding element. These systems function by allowing the penetrating enhancers to pass through the barrier layer of the skin, and in a physically associated complex, bring all the components of the delivery system into the dermal layer of the skin. Once in the dermal layer of the skin, the vasodilators act to expand or dilate the capillaries and other blood vessels in and beneath the dermal layer, resulting in an increase in blood flowing into and away from the site of system application. The purpose of the polymeric binding element is not only to provide a binding agent, but also to function as a delivery vehicle for the transdermal release of the vasodilator and active drug molecule, post stratum corneum penetration.

However, polymeric binding elements have a substantial molecular weight, which may inhibit or retard their ability to penetrate the skin. Secondly, alcohol soluble vasodilators and alcohol soluble active drug molecules can be difficult to associate with some binding elements in a mixture. Finally, as a result of the physical and chemical properties of some polymeric binding elements, they can act as thickening agents in the solution, which may not be desirable in certain applications.

It is therefore an object of the present invention to provide a transdermal drug transport system that efficiently and easily allows for the effective delivery of a broad range of active drug ingredients through the skin and into the blood supply of a living organism, including animals and humans, without the use of a polymeric binding element.

SUMMARY OF THE INVENTION

The problems of the prior art have been overcome by the present invention, which provides an efficient, predictable and reliable active ingredient transdermal delivery system for one or more active ingredients. More specifically, the present invention combines functional elements of the transdermal drug delivery system that can perform in more than one functional capacity to achieve the results of delivering a drug or therapeutic or diagnostic agent through the skin and into the bodily fluids. The present invention utilizes the solubility of the active drug molecule and/or the vasodilator and creates a mixture where the active drug molecule is dissolved into a solvent, the vasodilator is dissolved into a solvent which may be the same or different from the solvent used for the active drug molecule, and a penetration enhancer is added to the mixture but is not necessarily bound to either the active ingredient or the vasodilator. The need for a polymeric binding agent is eliminated, thus diminishing the total molecular weight of the mixture and increasing the penetration and delivery efficiency of selected active ingredients, including but not limited to drugs.

DETAILED DESCRIPTION OF THE INVENTION

The invention comprises the creation of a molecular transdermal complex that performs the following functions:

1) dermal penetration; 2) vasodilation and 3) delivery of the active drug molecule or agent into the bodily fluids (e.g., into the blood or into the skin tissue). The functional characteristics of the component molecular parts of the complex can be shared within any one or more of the component molecular parts of the complex with the eventual result being the transdermal delivery of an active drug molecule or agent into the bodily fluids or tissues of a living organism. The functional sharing between the delivery complex components may result from a naturally diverse molecule or it may result from a physical modification of an existing molecule to intentionally incorporate the desired traits into a component molecule. Examples of this functional sharing include, but are not limited to, a vasodilator compound serving also as an active drug molecule, a vasodilator serving also as a penetration agent, a vasodilator serving also as a binding agent, a penetration agent serving also as an active drug agent, and a penetrating agent serving also as a binding agent.

Examples of chemical vasodilators include, and are not limited to, acetylcholine, amrinone, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di-isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, methyl salicylate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, xanthinol nicotinate, diazoxide, hydralazine, minoxidil and sodium nitroprusside. Centrally acting agents include clonidine, quanaberz and methyl dopa. Alpha-adrenoceptor blocking agents include indoramin, phenoxybenzamine, phentolamine and prazosin. Adrenergic neuron blocking agents include bedmidine, debrisoquine and guanethidine. ACE inhibitors include benazepril, captopril, cilazapril, enalapril, fosinopril, lisinopril, perindopril, quinapril and ramipril. Ganglion-blocking agents include pentolinium and trimetaphan. Calcium channel blockers include amlodipine, diltiazem, felodipine, isradipine, nicardipine, nifedipine, nimodipine and verapamil. Prosteglandins include prostacyclin, thrombuxane $A_2$, leukotrienes, PGA, $PGA_1$, $PGA_2$, $PGE_1$, $PGE_2$, PGD, PGG and PGH. Angiotension II analogs include saralasin. Other vasodilators include nitroglycerin, labetalol, thrazide, isosorbide dinitrate, pentaerythritol tetranitrate, digitalis, and diazoxide. This element may serve exclusively as the vasodilation agent or it may also serve another function to the delivery complex such as the penetration agent or the active drug agent. One or more vasodilators or chemically modified vasodilators may be used in the delivery complex at any one time for one formulation for the purpose of transdermally delivering an active drug molecule or agent. The delivery complex may contain one or more different vasodilators in the same complex to achieve varying and different degrees and modes of vasodilation.

The second element of the delivery complex is an ingredient that functions as a permeation or penetration enhancer. Suitable enhancers include but are not limited to vegetable oil, oleic acid, aliphatic chained lipids, cholesterol, a vegetable oil/alcohol mix, or combinations thereof including, but not limited to, various compositions and preparations of liposomes. Suitable vegetable oils include hamamelis, peanut oil, olive oil, sunflower oil, soybean oil, monoi oil and macadamia oil, with olive oil being preferred. Suitable alcohols for the vegetable oil/alcohol mix include ethyl alcohol, isopropyl alcohol and methanol. Olive oil mixed with isopropyl alcohol is a preferred vegetable oil/alcohol mix. Eucalyptol is a further suitable example of a vegetable oil/alcohol mix. Suitable ratios of vegetable oil:alcohol range from about 5:1 to about 1:10, preferably 1:2. Suitable amounts of vegetable oil or vegetable oil/alcohol mix in the delivery complex range from about 1% to about 66% by weight, more preferably from about 10% to about 33.3% by weight. This component may serve exclusively as the penetrating agent or it may also serve another function to the delivery complex such as the vasodilator or as the active drug agent. One or more penetrating agents or chemically modified penetrating agents may be used in varying quantities or ratios with respect to the other component parts in the drug delivery complex at any one time. The third element of the delivery complex is the active ingredient. The term "active ingredient" is used herein to indicate any material or composition desired to be delivered transdermally, especially therapeutic drugs and molecules and diagnostic agents. This element may serve exclusively as the active drug agent or it may also serve another function to the delivery complex such as vasodilation or penetration. Examples of active ingredients that can be used in accordance with the present invention include, but are not limited to, acebutolol, acetaminophen, acetohydoxamic acid, acetophenazine, acyclovir, adrenocorticoids, albuterol, alendronate, allopurinol, alprazolam, alpha hydroxylipids, aluminum hydroxide, amantadine, ambenonium, amiloride, amino acids and amino acid polymers, aminobenzoate potassium, amiodarone HCl, amitriptyline, amobarbital, amlodipine, amoxicillin, amphetamine, ampicillin, amoxapine, androgens, anesthetics, antibody molecules, anticoagulants, anticonvulsants-dione type, antisense molecules, antithyroid medicine, appetite suppressants, aspirin, astemizole, atenolol, atorvastatin, atropine, azatadine, azithromycin, bacampicillin, baclofen, beclomethasone, belladonna, benzazepril, bendroflumethiazide, benzoyl peroxide, benzthiazide, benztropine, betamethasone, betha nechol, betaxolol HCl, biperiden, bisacodyl, bisoprolol/HCTZ, bleomycin, botulism toxin, bromocriptine, bromodiphenhydramine, brompheniramine, buclizine, budesonide, bumetanide, bupropion HCl, buspirone, busulfan, butabarbital, butanol, butaperazine, butoconazole nitrate, butorphanol, caffeine, calcitonin, calcium carbonate, camptothecin, capsaicin, captopril, carbamazepine, carbenicillin, carbidopa & levodopa, carbinoxamine inhibitors, carbonic anhydrase, carboplatin, carisoprodol, carotene, carphenazine, carteolol HCl, cascara, cefaclor, cefproxil, cefuroxime, cephalexin, cephradine, cetirizine, chlophedianol, chloral hydrate, chlorambucil, chloramphenicol, chlordiazepoxide, chloroquine, chlorothiazide, chlorotrianisene, chlorpheniramine, chlorpromazine, chlorpropamide, chlorprothixene, chlorthalidone, chlorzoxazone, cholestyramine, cimetidine, cinoxacin, ciprofloxacin, cisapride, cis-platin, clarithromycin, clemastine, clidinium, clindamycin, clofibrate, clomiphere, clonazepam, clonidine, clorazepate, clotrimoxazole, cloxacillin, cloxapine, codeine, colchicine, collagen, coloestipol, conjugated estrogen, contraceptives, corticosterone, cortisone, crornolyn, cyclacillin, cyclandelate, cyclizine, cyclobenzaprine, cyclophosphamide, cyclothiazide, cycrimine, cyproheptadine, cytokines, danazol, darithron, dantrolene, dapsone, daunorubicin, deoxyribonucleic acid, desipramine-HCl, desloratadine, desogestrel, dextroamphetamine, dexamethasone, dexchlorpheniramine, dextromethorphan, diazepan, diclofenac sodium, dicloxacillin, dicyclomine, diethylstilbestrol, diflunisal, digitalis, digoxin, diltiazen, dimenhydrinate, dimethindene, diphenhydramine, diphenidol, diphenoxylate & atrophive, diphenylopyraline, dipyradamole, dirithromycin, disopyramide, disulfiram, divalporex, docusate calcium, docusate potassium, docusate sodium, dopamine, domiphen bromide, doxazosin, doxorubicin, doxylamine, dronabinol, enzymes, enalaprilat, ephedrine, epinephrine, ergoloidmesylates, ergonovine, ergotamine, erythromycins, erythropoietin, conjugated estrogens, estradiol, estrogen, estrone, estropipute, etbarynic acid, etchlorvynol, ethinyl estradiol, ethopropazine, ethosaximide, ethotoin, etidronate sodium, etodolac, famotidine, felodipine SR, fenoprofen, fenoterol, fentanyl, ferrous fumarate, ferrous gluconate, ferrous sulfate, fexofenadine, finasteride, flavoxate, flecaimide, fluconazole, fluoxetine, fluphenazine, fluprednisolone, flurazepam, fluticasone, fluticasone propionate, fluvastin, fluvoxamine maleate, formoterol fumarate, folic acid, fosinopril, furosemide, gabapentin, ganciclovir, gemfibrozil, glimepiride, glipizide, glyburide, glycopyrrolate, gold compounds, granstronHCl, griseofuwin, growthhormones, guaifenesin, guanabenz acetate, guanadrel, guanethidine, guanfacine, halazepam, haloperidol, heparin, hetacillin, hexobarbital, hydralazine, hydrochlorothiazide, hydrocodone with APAP, hydrocortisone (cortisol), hydroflunethiazide, hydroxychloroquine, hydroxyzine, hyoscyamine, ibuprofen, imipramine, idebenone, indapamide, indomethacin, isradipine, insulin, interferon, ipratropiumbromide, iofoquinol, iron-polysaccharide, isoetharine, isoniazid, isopropamide, isoproterenol, isosorbide mononitrate S.A, isotretinoin, isoxsuprine, isradipine, itraconazole, ivermectin, kaolin & pectin, ketoconazole, ketoprofen, ketorolac-tromethamine, lactulose, lansoprazole, latanoprost, levodopa, levaflozacin, levonogestrel levothyroxine, lidocaine, lincomycin, liothyronine, liotrix, lisinopril, lithium, lomefloxacin HCl, loperamide, loracarbef, loratadine, lorazepam, losartan, losartan/HCTZ, lovastatin, loxapine succinate, lymphokines, magnesium hydroxide, magnesium sulfate, magnesium trisilicate, maprotiline, meclizine, meclofenamate, medroxyprogesterone, mefloquine HCl, melatonin, melenamic acid, meloxicam, melphalan, menthol, mephenytoin, mephobarbital, meprobanate, mercaptopurine, mesoridazine, metaproterenol, metaxalone, metformin hydrochloride, methadone, methamphetamine, methaqualone, metharbital, methenamine, methicillin, methocarbamol, methotrexate, methsuximide, methylchlothinzide, methylcellulose, methyldopa, methylergonovine, methylphenidate, methylprednisolone, methylsergide, methyl salicylate, metformin HCl, metoclopramide, metolazone, metoprolol, metronidazole, mexiletine, miconazole nitrate, minoxidil, misoprostol, mitotane, moclobemide, moexipril HCl, mometasone, monamine oxidase inhibitors, morphine, mupirocin, nabumetone, nadolol, nafazodone, nafcillin, nalidixic acid, naproxen, narcotic analgesics, nedocromil sodium, nefazodone HCl, neomycin, neostigmine, niacin, nicardipine, nicotine, nifedipine, nimodipine, nitrazoxanide, nitrates, nitrofurantoin, nitroglycerin, nizatidine, nomifensine, norethindrone, norethindrone acetate, norfloxacin, norgestimate, norgestrel, nylidrin, nystatin, oflaxacin, omeprazol, orphenadrine, oxacillin, oxaprozin, oxazepam, oxprenolol, oxycodone, oxymetazoline, oxyphenbutazone, pancrelipase, pantothenic acid, papaverine, para-aminosalicylic acid, paramethasone, paregoric, paroxetine, pemoline, penicillamine, penicillin, penicillin-v, pentazocine HCl, pentobarbital, pentokifylline, peptides and peptide fragments, pergolid mesylate, perphenazine, pethidine, phenacetin, phenazopyridine, pheniramine, phenobarbital, phenolphthalein, phenprocoumon, phensuximide, phentolamine mesylate, phenylbutazone, phenylephrine, phenylpropanolamine, phenyl toloxamine, phenytoin, pilocarpine, pindolol, piper acetazine, piroxicum, poloxamer, polycarbophilcalcium, calcium polythiazide, potassium supplements, pravastatin, prazosin, prednisolone, prednisone, primidone, probenecid, probucol, procainamide, procarbazine, prochlorperazine, procyclidine, progesterone, promazine, promethazine, propantheline, propofol, propoxyphene, propranolol, proteins and protein fragments, pruzepam, pseudoephedrine, psoralens, psyllium, pyrazinamide, pyridostigmine, pyrodoxine, pyrilamine, pyrvinium, quinapril, quinestrol, quinethazone, quinidine, quinine, rabeprazole, ramipril, ranitidine, rauwolfia alkaloids, riboflavin, ribonucleic acid, rifampicin, risperidone, ritodrine, salicylates, salmeterol, sannosides a & b, scopolamine, secobarbital, senna, serotonin, sertraline, sildenafil citrate, simethicone, simvastatin, sodium bicarbonate, sodium phosphate, sodium fluoride, sodium nitrate, spironolactone, sucrulfate, sulfacytine, sulfamethoxazole, sulfasalazine, sulfinpyrazone, sulfisoxazole, sulindac, sumatriptan, talbutal, tamoxifen, tamazepam, tenoxicam, terazosin, terbinafine, terbutaline, terconzaole, terfenadine, terphinhydrate, tetracyclines, testosterone and analogs, thiabendazole, thiamine, thioridazine, thiothixene, thonzonium bromide, thyroglobulin, thyroid, thyroxine, tibolone, ticarcillin, timolol, tioconazole, tobramycin, tocainide, tolnaftate, tolazamide, tolbutamide, tolmetin, tramadol, trazodone, tretinoin, triamcinolone, triamterine, triazolam, trichlormethiazide, tricyclic antidepressants, trihexethyl, trifluoperazine, triflupromazine, trihexyphenidyl, trimeprazine, trimethobenzamine, trimethoprim, trimipramine, tripclennamine, triprolidine, troglitazone, trolamine salicylate, tumor necrosis factor, valacyclovir, valproic acid, valsartan, venlafaxine, verapamil, vitamin A, vitamin B-12, vitamin C, vitamin D, vitamin E, vitamin K, voltarin, warfarin sodium, xanthine, zidovudine, zopiclone and zolpidem. One or more active ingredients may be used in the same formulation for delivery. The active ingredient may serve exclusively as the active drug molecule or it may also serve as the vasodilator or the penetrating agent where the active drug molecule exhibits both functions in the drug delivery complex.

The drug delivery complex is in part created by predetermining the solubility of the various components. For example, if the active drug molecule or molecules to be used are soluble in alcohol, water or oil (lipid), it or they are dissolved in the suitable respective solvent. Similarly, if the vasodilator to be used is alcohol, water or oil soluble, it is dissolved in the suitable solvent, which can be the same or different from the solvent used to dissolve the active drug molecule(s). Suitable alcohol solvents include but are not limited to isopropanol, ethanol, methanol, or mixtures thereof. Suitable oil solvents include but are not limited to vegetable oils, such as olive oil, peanut oil, soybean oil, monoi oil, macadamia oil and sunflower oil; glycerin; cetyl alcohol and propylene glycol. The amount of solvent used may range from about 1% to 60% by weight. The two are then combined, and a penetration enhancer, which is preferably lipid-based, is then added to the mixture (the penetration enhancer may or may not be soluble). The order of the addition of the complex components may also change, depending on the desired formulation. For example, the water-soluble phase may be combined with the oil phase into an emulsion, then the alcohol phase added to the water-oil phases.

It is not necessary that the active ingredient(s) and vasodilator both be soluble in the same solvent. For example, if an active ingredient is used that is alcohol soluble, a vasodilator that is water soluble can be used. Each is dissolved in its respective solvent and then combined. Similarly, if the active ingredient is water soluble and the vasodilator is alcohol soluble, again each is dissolved in its respective solvent and combined. The penetration enhancer is then added. Other ingredients may be added to the mixture to achieve maximum delivery efficiency or other effects if desired.

The order of addition of the various components may be variable for each different formulation and delivery objective. The penetration enhancer/solvent mix may be added to the water and water soluble components (or vice versa), and then the alcohol soluble components may be added to the resulting mixture (or vice versa).

Although the described delivery complex transports drug molecules efficiently without any patch-like device, in some instances a patch may be desirable. Patches, pre-impregnated with one or more components of the delivery complex or with the complete delivery complex may be preferable for the delivery of some active drugs to facilitate delivery efficiency or to alter delivery kinetics or dynamics. If a patch is used in conjunction with the delivery complex of the present invention, preferably the patch is a non-breathable layer into which the complex components or the complex is placed or integrated. Suitable non-breathable layers include sheets of plastic, polyethylene, polyvinyl chloride, wax paper, foil, latex, etc., and combinations thereof. Those skilled in the art will recognize that any non-breathable substance (defined as a substance that does not allow the exchange of gases through its membrane) that is not deleterious to the particular active ingredient (s) or to the other delivery system components and that does not cause any irritation to the skin may be used. The patch-like device may function to create and control a suitable microenvironment at the drug delivery site to facilitate the delivery of drugs across the skin and into the bodily fluids. Environmental conditions which can be deleterious to transdermal drug delivery and which may be enhanced when the delivery system is combined with or applied by a patch-like device include: cold, heat, excessive humidity, dry skin or arid conditions. The patch-like like device may potentially maintain more stable and more favorable conditions (e.g., temperature, humidity, skin pore size, enhanced localized blood flow) for the optimization of transdermal drug transportation at the drug delivery site. The patch-like device may be secured to the skin by any suitable means, such as with a bandage having adhesive or fasteners. In the preferred embodiment, no adhesive is used, instead compression is used as discussed in detail below.

FORMULATION EXAMPLE 1

Separately, propylene glycol and water are combined and then mixed with olive oil. Ethanol, menthol and Loratadine are combined and added to the water/propylene glycol/olive oil mix. The amount of each component in the final formulation is as follows:

Olive oil-9%
Propylene glycol-2.5%
Water-38.5%
Ethanol-30%
menthol-10%
Loratadine-10%

FORMULATION EXAMPLE 2

Propylene glycol and water are combined and then mixed with oleic acid. To that mixture is added a mixture of isopropanol, menthol and ketoprofen. The amount of each component in the final formulation is as follows:

Oleic acid-15%
Propylene glycol-5%
Water-20%
Isopropanol-30%
menthol-10%
Ketoprofen-20%

What is claimed is:

1. A transdermal delivery system for delivering an active ingredient through the skin of a living body, consisting essentially of:
   a) an active ingredient;
   b) a vasodilator; and
   c) a permeation enhancer for enhancing the permeation of said active ingredient through said skin, wherein said active ingredient, vasodilator and permeation enhancer are dissolved in a common solvent.

2. The transdermal delivery system of claim 1, wherein said solvent is an alcohol or water.

3. The transdermal delivery system of claim 2, wherein said alcohol is selected from the group consisting of isopropanol, ethanol, methanol and mixtures thereof.

4. The transdermal delivery system of claim 1, wherein said solvent is selected from the group consisting of olive oil, peanut oil, soybean oil, monoi oil, macadamia oil sunflower oil, glycerin, cetyl alcohol and propylene glycol.

5. The transdermal delivery system of claim 1, wherein the amount of said solvent ranges from about 1% to 60% by weight.

* * * * *